United States Patent
Scholz

(10) Patent No.: US 7,278,628 B2
(45) Date of Patent: Oct. 9, 2007

(54) DEVICE FOR THE DOSING OF GASEOUS AND/OR VAPOROUS MATTERS

(75) Inventor: Christian Scholz, Berlin (DE)

(73) Assignee: MSA Auer GmbH, Berlin (DE)

( * ) Notice: Subject to any disclaimer, the term of this patent is extended or adjusted under 35 U.S.C. 154(b) by 370 days.

(21) Appl. No.: 10/503,561

(22) PCT Filed: Jan. 30, 2003

(86) PCT No.: PCT/DE03/00286

§ 371 (c)(1),
(2), (4) Date: Aug. 3, 2004

(87) PCT Pub. No.: WO03/066114

PCT Pub. Date: Aug. 14, 2003

(65) Prior Publication Data

US 2005/0082695 A1  Apr. 21, 2005

(30) Foreign Application Priority Data

Feb. 4, 2002 (DE) ................................. 102 04 496

(51) Int. Cl.
*B01F 3/04* (2006.01)
(52) U.S. Cl. .......................... 261/26; 261/95; 261/96; 261/DIG. 88
(58) Field of Classification Search ............... 261/79.2, 261/DIG. 88, 26, 95, 96
See application file for complete search history.

(56) References Cited

U.S. PATENT DOCUMENTS 3,795,438 A   3/1974 Kristiansen et al.
5,198,451 A * 3/1993 Andersen et al. ............ 514/330
5,565,148 A   10/1996 Pendergrass, Jr.
5,898,475 A   4/1999 Martin
6,371,451 B1 * 4/2002 Choi ............................ 261/26

FOREIGN PATENT DOCUMENTS

| DE | 2139168 | 12/1971 |
| DE | 19916967 | 5/2001 |
| WO | WO00/05330 | 2/2000 |
| WO | WO 0053301 | 9/2000 |
| WO | WO 0130404 | 3/2001 |

* cited by examiner

*Primary Examiner*—Robert A. Hopkins
(74) *Attorney, Agent, or Firm*—Wood, Phillips, Katz, Clark & Mortimer

(57) ABSTRACT

Apparatus for dosing gaseous and/or vaporous substances An apparatus for dosing gaseous and/or vaporous substances, in particular for generating varying scents, includes a multitude of packaged storage containers (1) from which different gases and/or vapors are driven out by a carrier medium. On their inlet sides, the storage containers are connected to a common carrier medium manifold (13) via a shut-off device (4) assigned to each storage container that can be actuated, and on their outlet sides to a joint homogenization chamber (8). Both the carrier medium manifold and the homogenization chamber are connected to a carrier medium source using a regulating valve (5, 9). Check valves (6, 7) are integrated in the gas passages to the storage container and from the storage container to the homogenization chamber. A dosing apparatus designed based on this principle is characterized by low space requirements and materially separate volume flows that can be exactly timed and dosed.

14 Claims, 4 Drawing Sheets

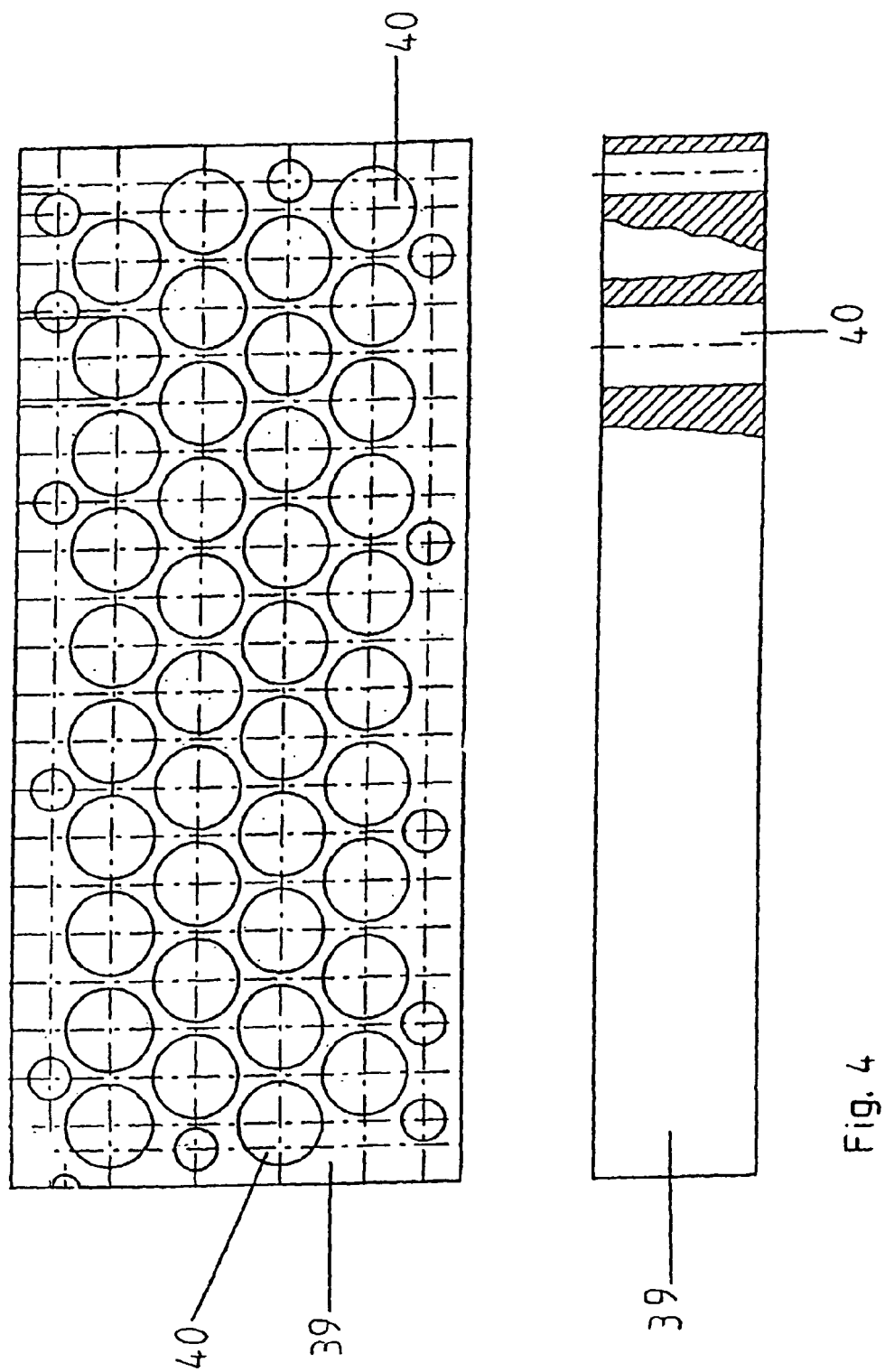

DEVICE FOR THE DOSING OF GASEOUS AND/OR VAPOROUS MATTERS

This invention relates to an apparatus for dosing gaseous and/or vaporous substances, particularly odorous substances, with at least one storage container in which the gas to be dosed is provided and which can be connected to a carrier medium that flows through it and drives a defined gas volume out at defined intervals.

To simplify matters, when referring to gaseous substances, these hereinafter shall include vapors.

DE 197 53 956 A1 describes a scent cartridge designed as a cylindrical hollow body that contains agents or scents bound by a carrier medium bound by a carrier medium. By applying a timed and/or volume-controlled gas flow such as air, carbon dioxide, nitrogen, or inert gas to the carrier material stored in the cylindrical storage container such as activated carbon, silica gel, or aluminum oxide a predefined volume of the respective material can be driven out at a specific point in time. The substance driven out is a scent sent out to people to match specific visual and/or acoustic impressions.

A known apparatus for delivering gaseous media, here in the form of scents, is described in EP 0611476 B1 and comprises various carriers of scents arranged on a roller-type magazine. The required scent carrier is loaded into a compressed air line at a junction by turning the roller magazine to drive the scent out of the carrier material and transport it via pipelines to the use area. While this apparatus is sophisticated and susceptible to failure, it also fails to ensure accurate timing and dosing of the respective gas flow, accurate separation of subsequent gas flows, and fast switching from one gas flow to another. Despite an arrangement of several storage rollers, it seems difficult to mix two or more substances and deliver them together. Tight sealing of the individual gas storage containers constitutes another problem. In addition, the known apparatus requires too much space.

It is therefore the problem of the invention to provide an apparatus for dosing gaseous and vaporous substances produced in a storage container that requires little space and is able to exactly time and dose such substances in fast succession while accurately separating subsequent gas streams.

This problem is solved according to the invention by the apparatus comprising the characteristics described in claim 1. The dependent claims disclose further characteristics and advantageous improvements of the invention.

In other words, the inventive idea of this invention is to connect a multitude of storage containers in which the gas to be driven out and dosed is produced to a central distribution unit for the carrier medium and to equip each storage container inlet with an upstream controllable shut-off element. This makes it possible to drive out accurately dosed volumes of gas in fast succession and at defined intervals. On their gas outlet sides, the storage containers are connected to a joint homogenization chamber that is also directly connected with the carrier medium source and a discharge line. The gas/carrier medium mixture introduced to the homogenization chamber from the storage container is homogenized and diluted by the separately introduced carrier medium stream so that the respective gas can be discharged in full and its full quantity arrives at its destination. As soon as the respective shut-off device in front of the storage container is closed and no more dosing gas flows into the homogenization chamber, the pure carrier medium can still be supplied to it and flush it so that no residual gas from the previous cycle is still in the chamber when the subsequent dosing cycle begins. This allows fast and accurate exchange of gases without undesirable mixing of different gases. The homogenization chamber may also be used for intended mixing of different gases and for dosing such gas mixtures. The gases in the storage container can be produced by volatilizing the coating on a substrate or by reacting different substances in the storage container, both with and without heating, and used for dosing gaseous or vaporous substances in general, and, in a preferred embodiment, for producing different scents, for example to support the plot in a motion picture.

In an advantageous improvement of the invention, the storage containers designed as pipe-shaped hollow bodies are arranged between a flat carrier medium distributor plate and a homogenization chamber designed as a flat and even body. The carrier medium distributor plate comprises parallel transverse ducts with individual gas outlets to which the storage containers are connected and tightly sealed and that may be opened separately using shut-off facilities such as solenoid valves. The transverse ducts are connected by a joint longitudinal duct that is connected to a carrier medium source. On their outlet sides, the storage containers are connected to a homogenization chamber that is also connected to the carrier medium source. This design allows the arrangement, in parallel and at an offset, of a multitude of storage containers on very little space and to connect this arrangement simultaneously to a carrier medium source and the homogenization chamber. The space requirement of this apparatus is very small.

According to another important characteristic of the invention, the ends of the storage containers are sealed into recesses of receiving plates that sit close to, and are sealed against, the carrier medium distributor plate and the homogenization chamber.

It is another important characteristic of the invention that the gas passages into and out of the storage container are closed by one check valve each only, which is only opened by the open solenoid valve when carrier medium is supplied. In this way, the storage containers are always tightly sealed when no gas is driven out by the carrier medium. This allows exact dosing without any gas gushing out.

In an advantageous improvement of the invention, the carrier media volume flow is controlled using regulating valves, preferably proportional-action valves.

In an embodiment of the invention, the storage containers are elastically mounted into a support plate. In this way, many storage containers can be combined in a block, which makes replacing empty storage containers much easier.

Various inert gases can be used as carrier media. The use of fluids as carrier media is conceivable.

Other characteristics that represent aspects of the invention can be derived from the description below of an embodiment of the apparatus for producing different scents that accompany a feature presentation in a movie theater.

An embodiment of the invention is explained in greater detail below with reference to the figures. Wherein:

FIG. 4 shows a top view and a partially sectional side view of a mounting plate as an assembly aid for a multitude of storage containers.

Figure 1:
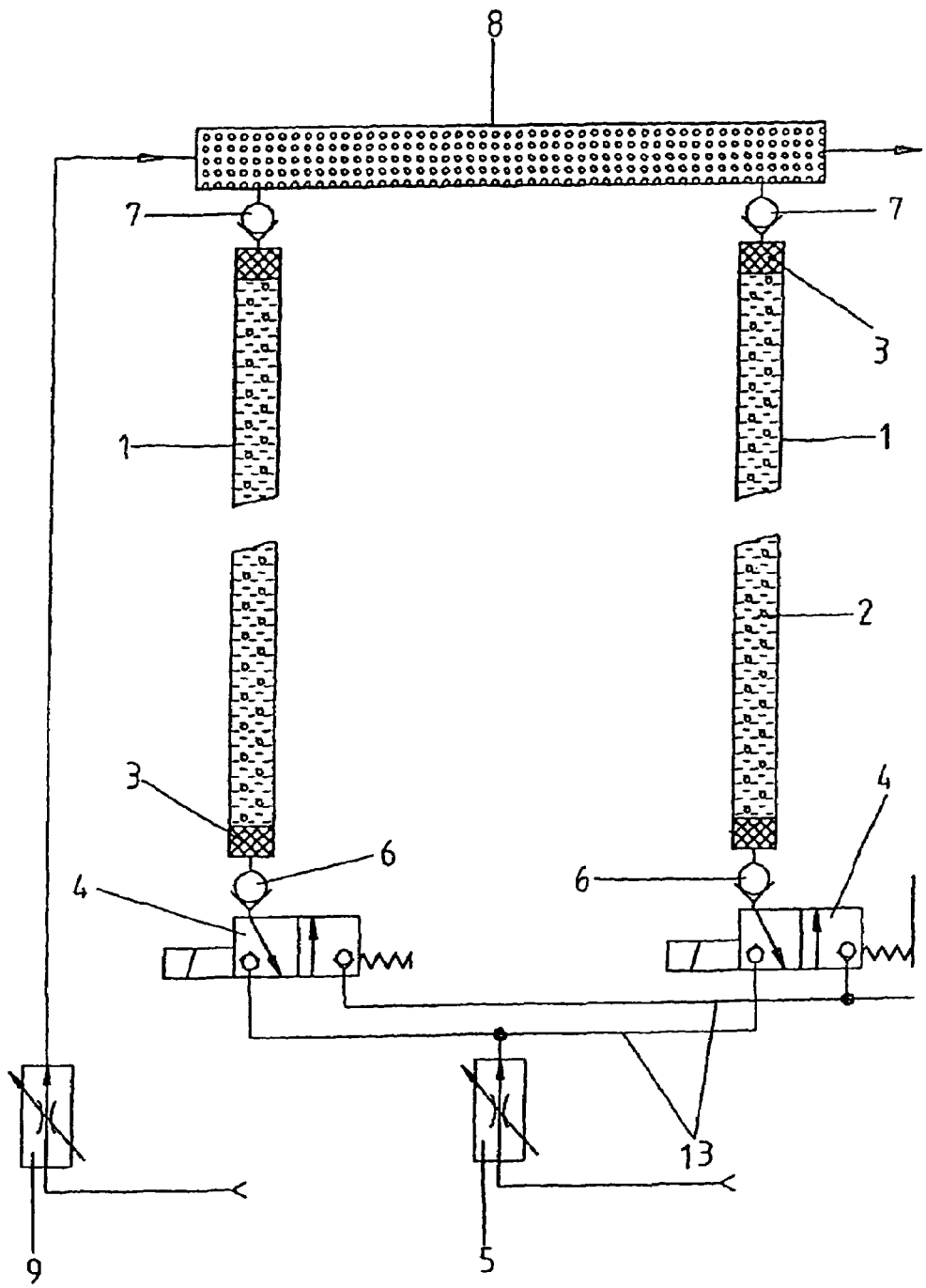
FIG. 1 shows a simplified block diagram of the operation of the apparatus according to the invention for selective dosing of various (here: two) gaseous substances.

The principle of operation of the apparatus according to the invention as shown in FIG. 1 is as follows: Storage containers 1 that consist of glass or another suitable material and are shown as small glass tubes in this embodiment are filled with a gas-forming agent 2, here with a substrate that has a large surface area such as activated carbon, aluminum oxide, or silica gel. To simplify matters, the block diagram shows just two storage containers 1. A practical design may also include a multitude of storage containers 1 arranged next to each other to require as little space as possible and providing different dosing media. A volatile substance to be dosed is adsorbed to the surface of the substrate. Alternatively, the storage container 1 may contain substances as gas-forming agents 2 that react with each other to produce a gas. The storage containers 1 that provide different gases are closed at both ends by a gas-permeable fixing element 3 that in this embodiment consists of a porous synthetic material. The storage containers 1 are connected on their inlet sides to a carrier medium source (not shown) via a check valve 2 and a controllable shut-off device 4 such as a solenoid valve, and via a first joint regulating valve 5 such as a proportional-action valve. Potential carrier media are gases such as compressed air, helium, or nitrogen, or fluids such as water, oils, bases, etc. FIG. 1 shows the controllable shut-off elements 4 in their closed position. The check valves 6 and 7 are closed. As soon as one—or optionally several—shut-off facilities are opened for a specific time based on a predefined program, the carrier medium flows at the rate set by the regulating valve 5 via a first check valve 6 into or through the storage container 1 and carries the dosing medium (gas or vapor) produced there or driven out of there via a second check valve 7 connected to the outlet side of the storage container 1 into a homogenization chamber 8. From a carrier medium source (not shown), a carrier medium is conducted via a second regulating valve 9 that may be a proportional-action valve or a manual valve into the homogenization chamber 8. It is preferred that the carrier medium supplied to the homogenization chamber 8 is identical with the carrier medium supplied to the storage container 1. In the homogenization chamber 8, the exactly set gas volume discharged from the storage container(s) in the time unit defined by the shut-off device 4 is received by the carrier media stream supplied via the second regulating valve 9, distributed and diluted in it and subsequently directed into a room as a scent or agent or supplied to a chemical process or a specific processing operation. If two or more gases are introduced into the homogenization chamber 8, this unit guarantees their intermixing, the gas or gas mixture to be dosed is completely discharged from the system, and dosing is accurate. This also means that the homogenization chamber 8 and downstream pipework are always well flushed so that no residues from the previous substance are absorbed in the new gas stream. This is vital when specific scents or agents are conducted into a room such as a movie theater in which various scents and mixtures of scents are to be produced in accordance with the varying images shown. The additional carrier medium stream and the regulating valve may be used to influence the intensity of the respective scent.

Figure 2:
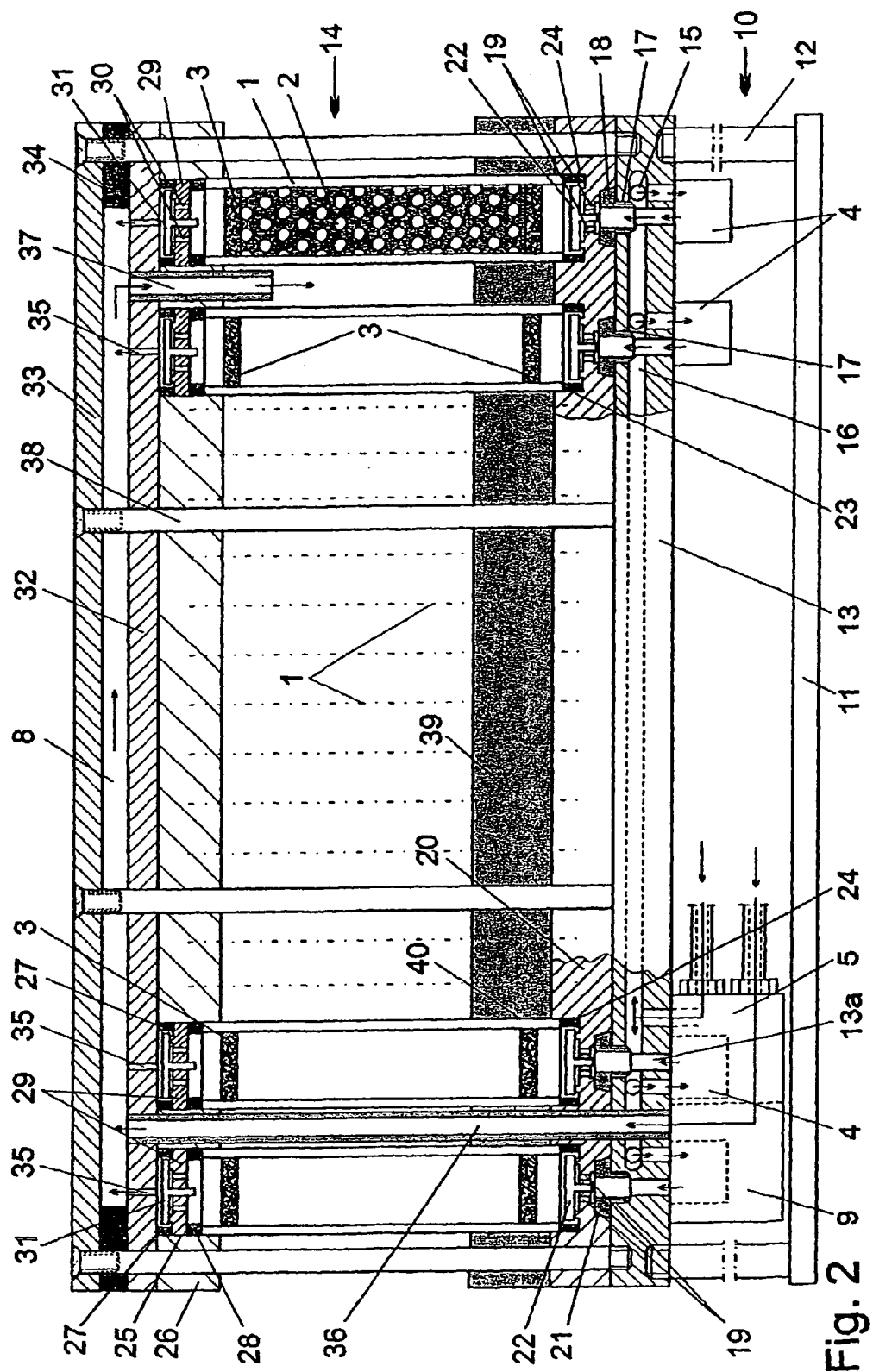
FIG. 2 shows a partly sectional view of an apparatus designed according to the principle of operation shown in FIG. 1.

FIG. 2 shows such a scent-producing system for a movie theater that is used to produce different scents that must vary fast and in accordance with the plot in a motion picture and any sudden changes of scene but remain clearly distinct. This gas dosing apparatus that produces scents is designed in such a way that it can be installed in the narrowest spaces such as in the arm rest of a viewer's seat in a movie theater, theater, and the like and can reproduce a great range of close-to-life aromas or scents, from pleasant forest, moss, hay, or flower scents, various food scents, to fire, exhaust fume and other unpleasant smells in fast succession.

According to FIG. 2, the scent-producing module in this embodiment includes a control unit 10 that is located between a base plate 11 and a carrier medium distributor plate 13 held at a spacing from the base plate by support columns 12, and a scent-producing unit 14 that mainly consists of a multitude of tube-shaped storage containers 1 compactly arranged in rows and columns and offset from each other on the carrier medium distributor plate 13, the homogenization chamber 8 being connected to the outlet sides of each of them.

Transverse ducts 15 run in parallel inside the carrier medium distributor plate 13 and are connected by a longitudinal duct 16. A carrier medium source (not shown) is connected to the longitudinal duct 16 via a first regulating valve (e.g. a proportional-action valve) 5. The carrier medium flows from a transverse duct 15 through the shut-off device (solenoid valve) 4 shown as a dashed line behind the regulating valves in FIG. 2, a gas passage 13a, a mushroom-shaped seal 18 held in a tapped hole 17 and comprising a central through hole, and two valve holes 19 in a first (bottom) receiving plate 20 that holds the bottom end of the storage container 1 into the storage container(s) 1. The generally conical heads of the mushroom-shaped seals 19 engage in an accordingly shaped recess 21 in the receiving plate 20, ensuring precise seating and tight sealing when the receiving plate 20 is mounted to the carrier medium distributor plate 13. The valve holes 19 formed in the first receiving plate 20 are closed by a spring-loaded flap 22 of the first check valve 6 that releases the valve holes 19 and thus allows the entry of the carrier medium into the respective storage container 1 when the shut-off element 4 is open. The tube-shaped storage container 1 is seated with its bottom open side in a cylindrical recess 23 in the receiving plate 20 on a ring gasket 24. On the opposite side, the end section of the storage container 1 is also held in a recess 25 of a second, upper receiving plate 26. A plate section 29, separate in this embodiment, with second valve holes 30 that are closed by a second flap 31 of the second check valve 7 is located between ring gaskets 27 and 28. The first and second check valves 6 and 7 are formed using the first and second valve holes 19 and 30 as well as the associated first and second valve plates 22 and 31 and ensure transport of the carrier medium that drives out the scents in one direction of flow while closing the container off in all other directions. The gas-forming agent 2 in the tube-shaped storage container 1 is silica gel to the surface of which different scents are adsorbed in different storage containers 1. The scent-coated substrate is held in the storage containers 1 by a fixing element 3 that is a porous PE frit in this embodiment.

The second (upper) receiving plate 26 is located behind the homogenization chamber 8 in the direction of flow of the scent-charged carrier medium. The homogenization chamber 8 is formed according to this embodiment of a bottom plate 32, a cover plate 33, and a seal 34 that runs around the perimeter along the rims of the bottom and cover plates. The bottom plate 32 is sealed against the second receiving plate 26 by its upper ring gaskets 27. The bottom plate 32 comprises two gas outlet holes 35 that are located in centered position above the second valve plates 31 of the second check valves 7. The surfaces of the bottom and upper plates 32, 33 that face each other have a special polished finish to let the scent-charged carrier medium flow without hindrance and not adhere to the inner surfaces of the homogenization chamber 8. The height of the interior space of the homogenization chamber 8 is determined by the thickness of the seal 34 and is very low as compared to the length and width of the system, so that the scent-charged carrier medium can be completely discharged from the homogenization chamber 8 and the homogenization chamber 8 can be flushed fast and without remnants by just a low, unscented carrier media stream when there is a change in clearly distinct scents and all shut-off elements 4 upstream of the storage containers 1 are closed.

The unscented carrier medium to be conducted to the homogenization chamber 8 for homogenizing and flushing is supplied via the second regulating valve 9 and a feed line 36 that runs directly into the homogenization chamber 8. It absorbs the scent stream from the storage container(s) 1, vortexes it and intermingles with it, dilutes it, and discharges it fast and without remnants from the homogenization chamber 8 so that the system can switch to the next scent without any residual scents prevailing. A discharge line 37 is provided at the outlet of the feed line 36 on the opposite side of the homogenization chamber through which the scent-charged carrier medium is carried off.

Figure 3:
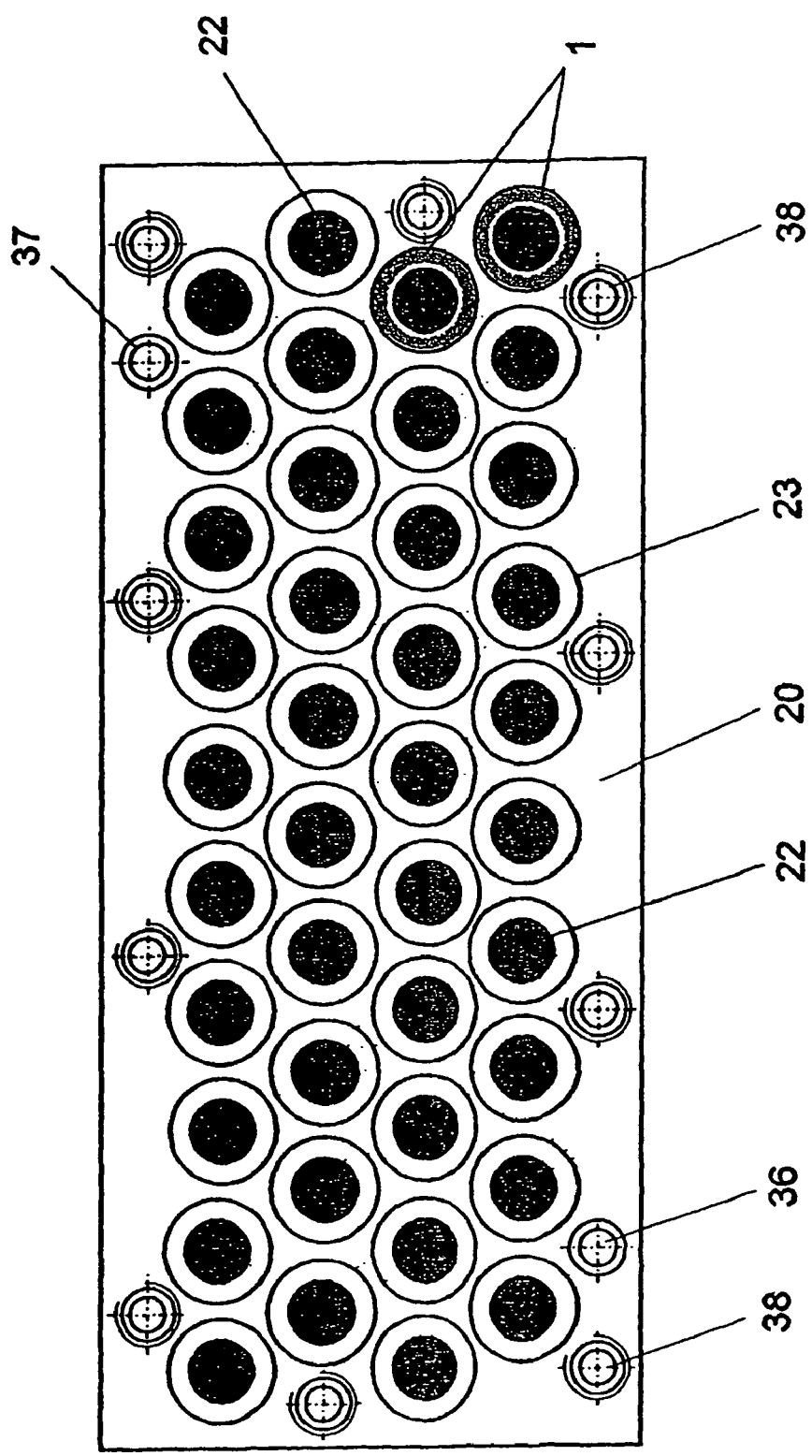
FIG. 3 shows a top view of a bottom receiving plate integrated in an apparatus according to FIG. 2 for connecting storage containers that provide the scents to a gaseous carrier medium.

After removing the cover plate 33 that is fastened on the rim of the carrier medium distributor plate 13 with stud bolts 38, the bottom plate 32 and the second (upper) receiving plate 26 can be detached to replace the storage containers 1 whose scent substrate is used up. The tube-shaped storage containers 1 are non-positively fixed in mounting holes 40 of a holding plate 39 because of its resilient material; the hole arrangement exactly matches the pattern of recesses 23, 25 in the receiving plates 20, 26. Furthermore, the holding plate 39 includes holes 41 in which the holding plate 39 is guided to the stud bolt 38. The holding plate 39 makes it possible to replace a complete set of storage containers 1 and to mount new storage containers 1 in the predefined grid. The grid of holes in the holding plate 39 as shown in FIG. 4 or the grid of cylindrical recesses 23 in the bottom receiving plate 20 (FIG. 3) also shows the offset arrangement of the tube-shaped storage containers 1. This arrangement can house a multitude of storage containers 1 in a highly compact space.

The invention claimed is:

1. An apparatus for dosing gaseous and/or vaporous substances with multiple storage containers that provide gas to be dosed and can be connected to a carrier medium that flows through it for driving out a defined gas/vapor volume at defined intervals, the apparatus comprising multiple storage containers having ends that close automatically against a direction of flow, inlet sides thereon being connected to a carrier medium manifold that has a controllable shut-off device for carrier medium assigned to each storage container and outlet sides thereon being connected to a homogenization chamber, wherein the homogenization chamber and the carrier medium manifold are independently connected to a carrier medium source, wherein the storage containers are tube-shaped hollow bodies for receiving the substances that form the dosing gas and are closed at both ends by a porous holding element, wherein first and second check valves are assigned to each side of the storage containers that open in the direction of flow when the carrier medium applies pressure and prevent the discharge of dosing gas from the storage container when the shut-off device is closed, and wherein the storage containers are sealed and held on both sides in recesses of lower and upper receiving plates, said recesses comprising valve holes for gas entry into the storage containers or the homogenization chamber that can be closed by flaps of the check valves.

2. The apparatus according to claim 1, wherein the carrier medium manifold is designed as a flat carrier medium distributor plate with parallel transverse ducts that are connected to the carrier medium source via a longitudinal duct, wherein each storage container is connected to the transverse ducts via gas passages and individually controllable shut-off facilities; wherein the homogenization chamber is a flat bottom plate with integrated gas passages; wherein the storage containers are arranged in parallel and at an offset from each other between the carrier medium distributor plate and the homogenization chamber and connected to gas passages.

3. The apparatus according to claim 2, wherein the carrier medium distributor plate and the homogenization chamber are equipped with a first regulating valve and a second regulating valve for separate control of the volume flow of the carrier medium.

4. The apparatus according to claim 1, wherein a mushroom-shaped seal with an axial hole is located between the lower receiving plate and the carrier medium distributor plate in the section between the gas passage and the first valve hole, a conical head of which protrudes into a conical recess in the receiving plate and a shaft of which is held in a tapped hole of the carrier medium distributor plate above the gas passage.

5. The apparatus according to claim 1, wherein a multitude of storage containers is arranged on a holding plate comprising mounting holes that elastically fix the storage containers and combined into a storage container unit, wherein the mounting holes are on the same axis as the gas passages and the recesses.

6. The apparatus according to claim 5, wherein the holding plate is made of an elastic material.

7. The apparatus according to claim 1, wherein the homogenization chamber comprises an inlet for pure carrier medium and an outlet for a mixture of carrier medium and gas to be dosed and wherein said inlet and outlet are provided on opposite ends of the homogenization chamber.

8. The apparatus according to claim 7, wherein the interior height of the homogenization chamber is determined by a seal that runs peripherally along the rims between a bottom plate and a cover plate of the homogenization chamber.

9. The apparatus according to claim 2, wherein stud bolts are placed along the rim of the carrier medium distributor plate that guide the receiving plates, the holding plate and the bottom and cover plates of the homogenization chamber while said cover plate is also screwed to them.

10. The apparatus according to claim 9, wherein the carrier medium distributor plate is braced with the cover plate of the homogenization chamber using a clamping device.

11. The apparatus according to claim 1, wherein the shut-off facilities and the regulating valves can be controlled according to a program.

12. The apparatus according to claim 1, wherein the apparatus is located in an area frequented by people to produce various scents.

13. The apparatus according to claim 12, wherein the apparatus is integrated into seating in a movie or dramatic theater or the like or connected to multiple seats via connecting pipes.

14. The apparatus according to claim 3, wherein the shut-off facilities and the regulating valves can be controlled according to a program.

* * * * *